Aug. 12, 1975 R. GROTUM Plant Pat. 3,763
POINSETTIA PLANT
Filed Aug. 19, 1974
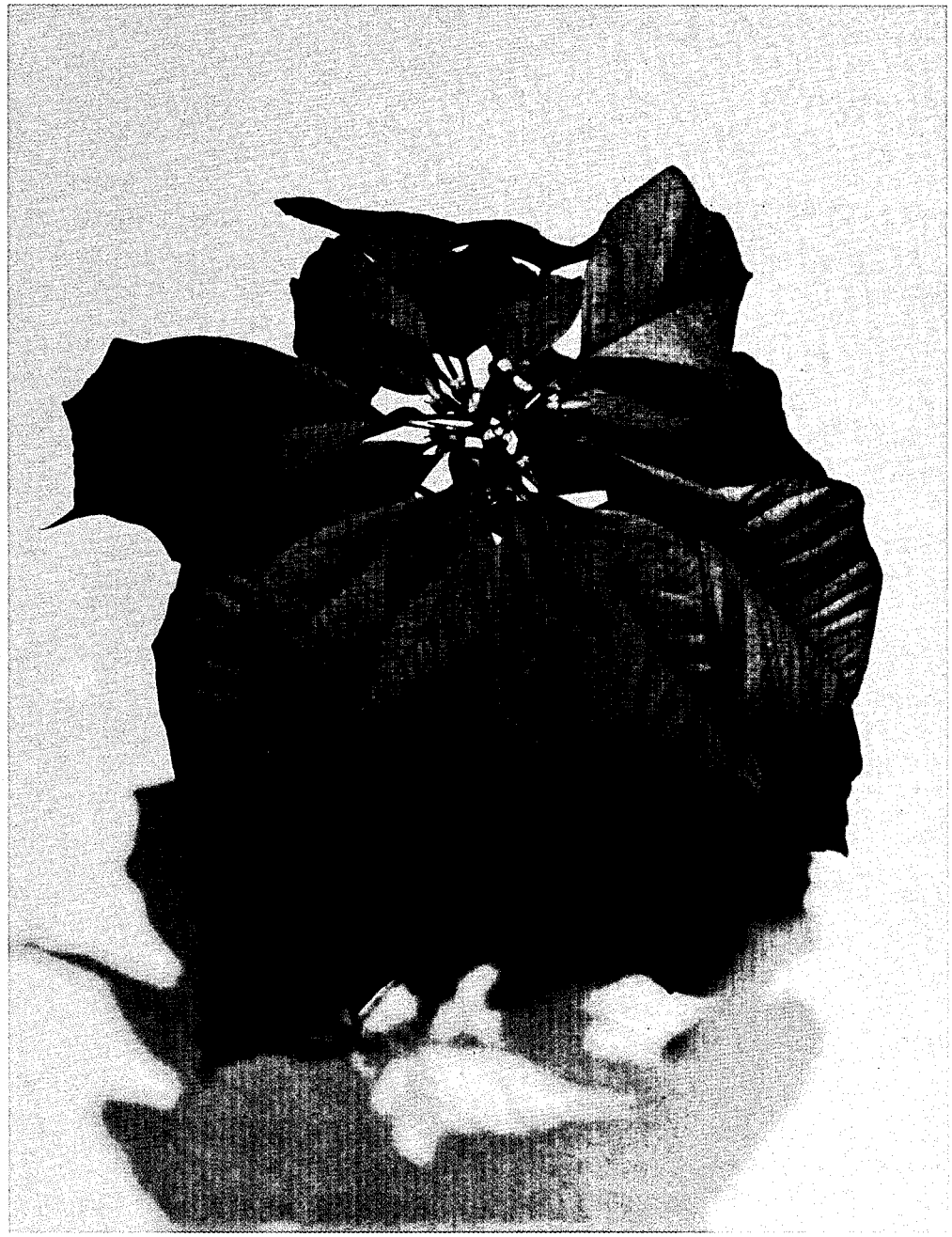

United States Patent

Plant Pat. 3,763

Patented Aug. 12, 1975

3,763

POINSETTIA PLANT

Rolf Grotum, Bendingbostel, Germany, assignor to Paul Ecke, Jr., Encinitas, Calif.

Filed Aug. 19, 1974, Ser. No. 498,725

Int. Cl. A01h *5/00*

U.S. Cl. Plt.—86 1 Claim

The present invention relates to a new and distinct variety of poinsettia plant (botanically known as *Euphorbia pulcherrima*) which was discovered by me as a bright brick red cultivated sport of the red poinsettia variety known as "Annette Hegg" (Plant Pat. No. 2,962), said discovery having been made by me in one of my greenhouses located at Bendingbostel, Germany.

At the time of my discovery aforesaid, I was growing in my greenhouses at Bendingbostel various poinsettia varieties, including many plants of the patented variety known as "Annette Hegg." In the course of these growing operations, my attention was attracted to one particular plant among those of "Annette Hegg" which bore bracts of a substantially earlier and different bright brick red color than the normal red bracts of "Annette Hegg." Close inspection of this particular plant showed that it had sported, so I carefully preserved the sport and kept it under close observation. In due course, I asexually reproduced the sport by vegetative cuttings taken therefrom and planted in my greenhouses at Bendingbostel. Continued observations and tests of the original sport and its progeny derived from the vegetative cuttings aforesaid and which have been propagated successfully through several generations, fully confirmed that the sport blooms about one week earlier than "Annette Hegg" and that their color comes true and remains very stable. While my observations and tests have shown that for all practical purposes, the new sport generally resembles the parent variety "Annette Hegg" except for its bract color, I have also found that the bright brick red bract color of the sport retains its brilliance much longer when the plants are grown in the home after removal from the greenhouse, than the bracts of "Annette Hegg" which tend to fade rather quickly. Also the bracts of the sport do not droop as much as those of "Annette Hegg" when the plants reach maturity.

The various characteristics and distinctions referred to above represent a unique and commercially valuable combination of features which distinguish the sport from its parent variety, as well as from all other poinsettia varieties of which I am aware, as evidenced by the following summary of characteristics which are outstanding in this new sport:

(1) A short-growing and compact plant habit;
(2) A uniform and fast rooting habit;
(3) A self-branching habit resulting in the production of multiple blooms without pinching off the terminal buds as required for other poinsettia varieties;
(4) Attractive green foliage which is darker green in color than the foliage of "Annette Hegg";
(5) Attractive, brighter brick red bracts that the normal red bracts of "Annette Hegg," said bracts having less tendency to doop than the bracts of "Annette Hegg" when the plants reach maturity, and the bright brick red color of the bracts being more stable and retaining their brilliance much longer when the plants are used for home decoration;
(6) Long-lasting plant qualities; and
(7) A distinctly earlier blooming habit than other standard Hegg varieties.

The accompanying drawing shows a typical specimen plant of my new poinsettia variety as depicted in color as nearly true as it is reasonably possible to make the same in a color illustration of this character.

Although the details of my new poinsettia sport, except for the principal differences referred to in the foregoing, are generally similar to those described in Plant Pat. No. 2,962, to which reference may be readily had, the following brief description is given for convenience, with color terminology in accordance with Wilson's Horticultural Colour Chart, except where general color terms of odinary dictionary significance are obvious:

PARENTAGE: Sport of "Annette Hegg" (Plant Pat. No. 2,962).

PROPAGATION: Holds its distinguishing characteristics through succeeding propagations by vegetative cuttings.

FORM: Short-growing; compact.

HABIT OF GROWTH: Self-branching; does not require pinching to produce multiple blooms.

ROOTING HABIT: Very uniform and very fast.

BLOOMING HABIT: An 8 to 8½-week variety.

BLOOMING SEASON: Blooms predictably and in the early part of the Christmas season; also good for flowering in spring, summer and autumn.

FOLIAGE:

Shape—Ovate, with some serration.

Color—Usually somewhat darker green than foliage of "Annette Hegg." New foliage—Upper side—Darker than Spinach Green, Plate 0960; lower side—darker than Spinach Green, Plate 0960/2. Old foliage—Upper side—Darker than Ivy Green, Plate 0001060; Lower side—darker than Ivy Green, Plate 0001060/2.

BRACTS: Relatively broad; retains brilliance longer and less drooping when mature than bracts of "Annette Hegg."

Color—Brick Red, from near Blood Red, Plates 820/3 to 820.

FLOWERS (Cyathia): Early; numerous; strong; little if any tendency to split; do not drop off prematurely.

REPRODUCTIVE ORGANS:

Stamens—Quite numerous; from about ⅛ inch to ¼ inch long. Color—Near Currant Red, Plate 821/2.

Pollen—Strong. Color—Near Canary Yellow, Plate 2.

Styles—Color—Near Currant Red, Plate 821/2.

Ovaries—Color—Near Scheele's Green, Plate 860.

Nectar cups—Color—Near Buttercup Yellow, Plate 5/1.

GENERAL OBSERVATIONS: While this new sport generally resembles the variety "Annette Hegg," it is principally distinguished therefrom by its somewhat darker green foliage color; brighter brick red bracts which retain their brillance much longer and with less tendency to fade when grown under the same conditions as "Annette Hegg"; less tendency of the bracts to droop when the plants reach maturity; and its distinctly earlier bloom than *other* standard Hegg varieties, usually maturing before Thanksgiving or the last week in November.

I claim:

1. A new and distinct variety of poinsettia plant, substantially as herein shown and described, characterized particularly as to novelty by the unique combination of a short-growing and compact plant habit, a uniform and fast rooting habit, a self-branching habit resulting in the production of multiple blooms without pinching off the terminal buds as required for other poinsettia varieties, attractive green foliage which is darker green in color than the foliage of "Annette Hegg," attactive brighter brick red bracts than the normal red bracts of "Annette Hegg," said bracts having less tendency to droop than the bracts of "Annette Hegg" when the plants reach maturity, and the bright brick red color of the bracts being more stable and retaining their brilliance much longer when the plants are used for home decoration, long-lasting plant qualities, and a distinctly earlier blooming habit than other standard Hegg varieties.

References Cited

UNITED STATES PATENTS

| | | | |
|---|---|---|---|
| P.P. 2,962 | 1/1970 | Hegg | Plants—86 |
| P.P. 3,160 | 5/1972 | Ecke | Plants—86 |
| P.P. 3,392 | 8/1973 | Ecke | Plants—86 |
| P.P. 3,394 | 8/1973 | Ecke | Plants—86 |

ROBERT E. BAGWILL, Primary Examiner